United States Patent
Mayer et al.

[11] Patent Number: 5,635,450
[45] Date of Patent: Jun. 3, 1997

[54] HERBICIDAL N-[(1, 3, 5-TRIAZIN-2-YL)-AMINOCARBONYL]-BENZENESULFONAMIDES

[75] Inventors: Horst Mayer, Ludwigshafen; Gerhard Hamprecht, Weinheim; Karl-Otto Westphalen, Speyer; Helmut Walter, Obrigheim; Matthias Gerber, Mutterstadt; Klaus Grossmann; Wilhelm Rademacher, both of Limburgerhof, all of Germany

[73] Assignee: BASF Aktiengesellschaft, Ludwigshafen, Germany

[21] Appl. No.: 500,450

[22] Filed: Jul. 12, 1995

Related U.S. Application Data

[62] Division of Ser. No. 220,459, Mar. 31, 1994, Pat. No. 5,478,798, which is a continuation of Ser. No. 39,222, filed as PCT/EP91/02192, Nov. 21, 1991, abandoned.

[30] Foreign Application Priority Data

Dec. 1, 1990 [DE] Germany ............ 40 38 430.6

[51] Int. Cl.$^6$ ............................................. C07D 251/42
[52] U.S. Cl. ............................................. 504/212; 544/211
[58] Field of Search ..................... 504/212; 544/211

[56] References Cited

U.S. PATENT DOCUMENTS 4,127,405 11/1978 Levitt ......................... 544/211

OTHER PUBLICATIONS

Mayer et al, Chemical Abstracts 117, Entry 69888 (1992).

*Primary Examiner*—John M. Ford
*Attorney, Agent, or Firm*—Keil & Weinkauf

[57] ABSTRACT

N-[(1,3,5-Triazin-2-yl)-aminocarbonyl]-benzenesulfonamide of the general formula

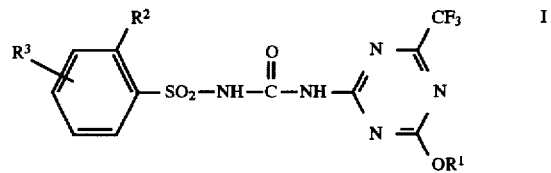

where $R^1$ is methyl or ethyl, $R^2$ is halogen, $C_1$-$C_3$-alkylsulfonyl, trifluoromethyl or 2-methoxyethoxy and $R^3$ is hydrogen, methyl, ethyl, methoxy, ethoxy, fluorine or chlorine, and their agriculturally useful salts, processes for their preparation and their use.

3 Claims, No Drawings

HERBICIDAL N-[(1, 3, 5-TRIAZIN-2-YL)-AMINOCARBONYL]-BENZENESULFONAMIDES

This is a divisional of application Ser. No. 08/220,459, filed Mar. 31, 1994 (now U.S. Pat. No. 5,478,798), which was a continuation of Ser. No. 08/039,222, filed Apr. 14, 1993, now abandoned, which is a 371 of PCT/EP 91/02192, filed Nov. 21, 1991.

The present invention relates to N-[(1,3,5-triazin-2-yl)-aminocarbonyl]-benzenesulfonamides of the general formula I

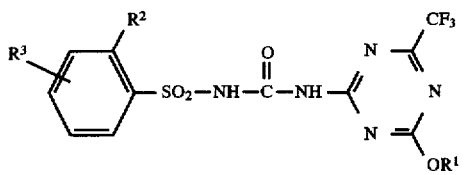

where $R^1$ is methyl or ethyl, $R^2$ is halogen, $C_1$-$C_3$-alkylsulfonyl, trifluoromethyl or 2-methoxyethoxy and $R^3$ is hydrogen, methyl, ethyl, methoxy, ethoxy, fluorine or chlorine, and agriculturally useful salts thereof.

The present invention furthermore relates to a process for the preparation of the compounds I and their use as herbicides.

U.S. Pat. Nos. 4,120,691 and 4,127,405 and EP-A 44 807 relate to sulfonylureas which have a herbicidal action and whose general formula embraces the compounds of the general formula I which are defined at the outset.

U.S. Pat. No. 4,120,691 describes the triazine compound A and the pyrimidine derivative B, these being the most closely related structures.

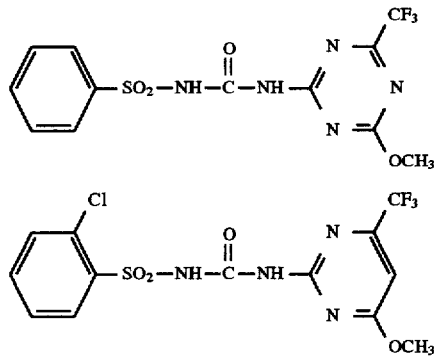

EP-A 44 807 describes two sulfonylureas C having an ortho allyloxy group.

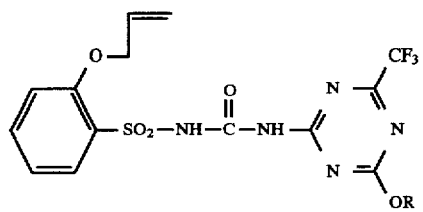

R=CH$_3$ or C$_2$H$_5$

EP-A 44 808 describes two sulfonylureas D having a 2-chloroethoxy substituent in the aromatic moiety.

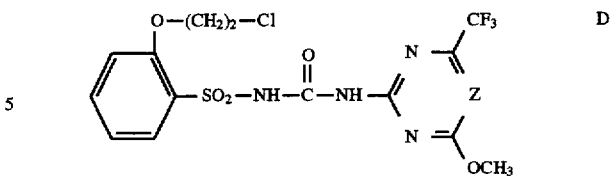

Z=CH or N

EP-A 48 143 mentions two N-methylated sulfonylureas E without characterizing them further.

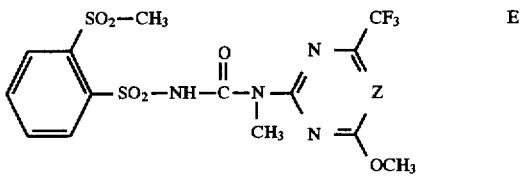

Z=CH or N

EP-A 388 873 relates to benzoates having the structure F.

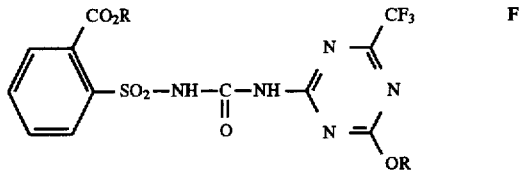

R=CH$_3$ or C$_2$H$_5$

U.S. Pat. No. 4,127,405 discloses sulfonylurea derivatives having chlorine or trifluoromethyl substitution in the ortho position of the phenyl ring and CH$_3$/OCH$_3$ substitution in the triazine ring

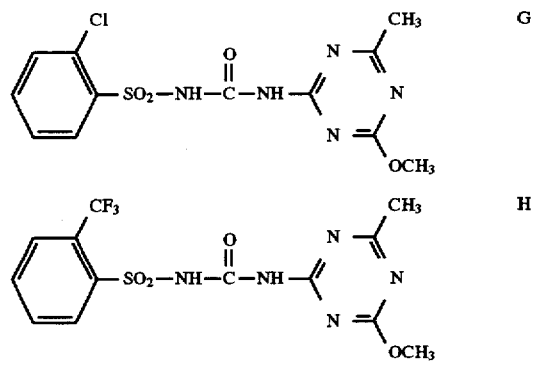

The compound G is known under the name chlorosulfuron (Glean®).

It is an object of the present invention to synthesize sulfonylureas which have improved properties compared with the known members of this herbicide class and are distinguished in particular by high selectivity in sensitive crops, such as rice or corn.

We have found that this object is achieved by the N-[(1, 3,5-triazin-2-yl)-aminocarbonyl]-benzenesulfonamides of the formula I which are defined at the outset.

In the formula I, $C_1$-$C_3$-alkylsulfonyl is methyl, -ethyl-, propyl- or isopropylsulfonyl and halogen is fluorine, chlorine, bromine or iodine, in particular fluorine or chlorine. Benzenesulfonamides in which $R^2$ is chlorine are particularly preferred.

The novel sulfonylureas of the formula I are obtainable by various methods which are described in the literature. Particularly advantageous methods (A–D) are described in detail below by way of example.

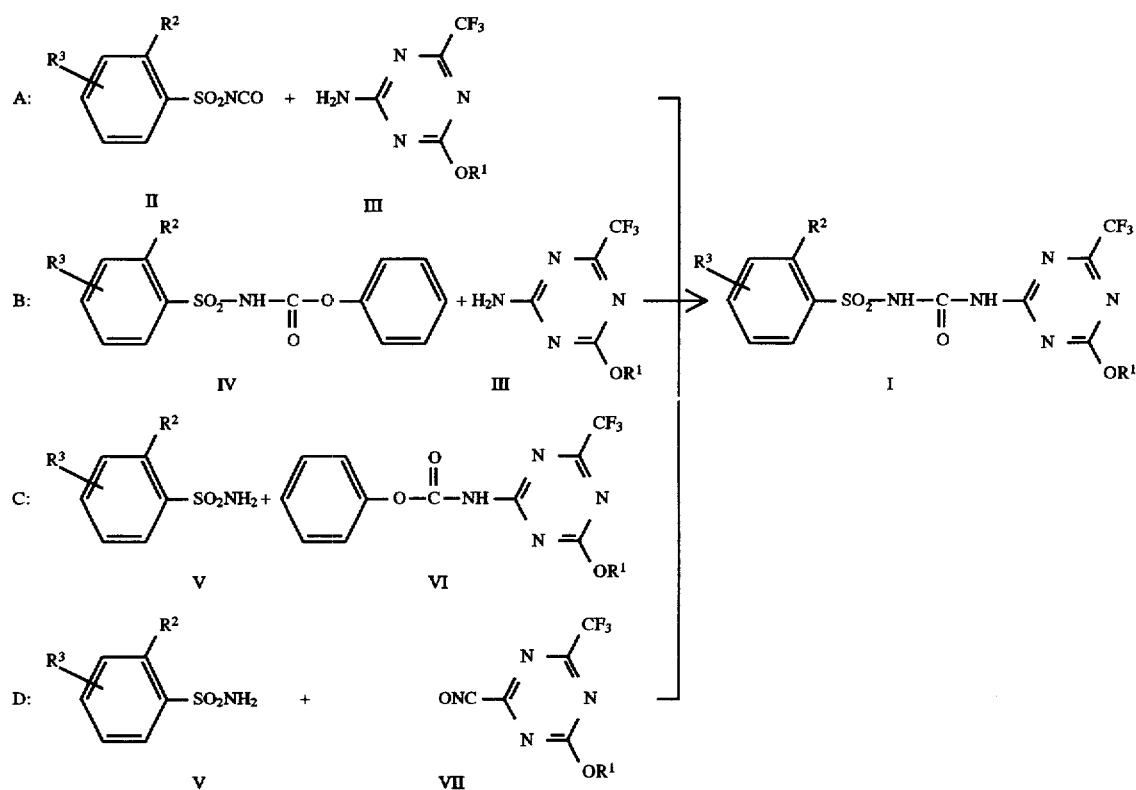

A: A sulfonyl isocyanate II is reacted in a conventional manner (EP-A-162 723) with about the stoichiometric amount of a 2-amino-1,3,5-triazine derivative III at from 0° to 120° C., preferably from 10° to 100° C. The reaction can be carried out continuously or batchwise under atmospheric or superatmospheric pressure (up to 50 bar), preferably at from 1 to 5 bar.

Solvents and diluents which are inert under the particular reaction conditions are advantageously used for the reactions. Examples of suitable solvents are halohydrocarbons, in particular chlorohydrocarbons, e.g. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, p- and m-dibromobenzene, o-, m- and p-chlorotoluene, and 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetol, cyclohexyl methyl ether, diethyl ether, ethylene glycol dimethyl ether, tetrahydrofuran, dioxane, thioanisole and β,β'-dichlorodiethyl ether; nitrohydrocarbons, such as nitromethane, nitroethane, nitrobenzene, o-, m- and p-chloronitrobenzene and o-nitrotoluene; nitriles, such as acetonitrile, butyronitrile, isobutyronitrile, benzonitrile and m-chlorobenzonitrile; aliphatic or cycloaliphatic hydrocarbons, e.g. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, e.g. ethyl acetate, ethyl acetoacetate and isobutyl acetate; amides, e.g. forms/aide, methylformamide and dimethylformamide; ketones, e.g. acetone and methyl ethyl ketone, and corresponding mixtures. The solvent is advantageously used in an amount of from 100 to 2,000, preferably from 200 to 700, % by weight, based on the starting material II.

The compound II required for the reaction is generally used in about an equimolar amount (for example in an amount of from 80 to 120%, based on the particular starting material III, of the stoichiometric amount). The starting material III may be initially taken in one of the abovementioned diluents and the starting material II added.

Advantageously, however, the process for the preparation of the novel compounds is carried out by a method in which the starting material II, if necessary in one of the abovementioned diluents, is initially taken and the starting material III is then added.

To complete the reaction, stirring is carried out for a further 20 minutes to 24 hours at from 0° to 120° C., preferably from 10° to 100° C., after the addition of the components.

A tertiary amine, e.g. pyridine, α,β,γ-picoline, 2,4- and 2,6-lutidine, 2,4,6-collidine, p-dimethylaminopyridine, trimethylamine, triethylamine, tri-n-propylamine, 1,4-diazabicyclo[2.2.2]octane [DABCO] or 1,8-diazabicyclo[5.4.0]undec-7-ene, can advantageously be used as a reaction accelerator in an amount of from 0.01 to 1 mol per mole of starting material II.

The end product I is isolated from the reaction mixture in a conventional manner, for example after distilling off the solvent or directly by filtration under suction. The remaining residue may furthermore be washed with water or dilute acid to remove basic impurities. However, the residue can also be dissolved in a water-immiscible solvent and washed in the manner described. The desired end products are obtained here in pure form; if necessary, they can be purified by recrystallization, stirring in an organic solvent which takes up the impurities or chromatography.

This reaction is preferably carried out in acetonitrile, methyl tert-butyl ether, toluene or methylene chloride in the presence of from 0 to 100, preferably from 0 to 50, mol equivalents of a tertiary amine, such as 1,4-diazabicyclo[2.2.2]octane or triethylamine.

B: A corresponding sulfonylcarbamate of the formula IV is reacted in a conventional manner (EP-A-120 814, EP-A-101 407) with a 2-amino-1,3,5-triazine derivative III in an inert organic solvent at from 0° to 120° C., preferably from 10° to 100° C. Bases, such as tertiary amines, may be added here, with the result that the reaction is accelerated and the product quality improved.

Suitable bases for this purpose are, for example, tertiary amines as stated under A, in particular triethylamine or 1,4-diazabicyclo[2.2.2]octane, in an amount of from 0.01 to 1 mol per mole of starting material IV.

Advantageously used solvents are those stated under A. The solvent is used in an amount of from 100 to 2,000, preferably from 200 to 700, % by weight, based on the starting material IV.

The compound IV required for the reaction is generally used in about an equimolar amount (for example in an amount of from 80 to 120%, based on the particular starting material III, of the stoichiometric amount). The starting material IV may be initially taken in one of the abovementioned diluents and the starting material III then added.

However, it is also possible initially to take the starting material III in one of the stated solvents or diluents and to add the sulfonylcarbamate IV.

In both cases, a base may be added as a catalyst before or during the reaction.

The end product I can be obtained from the reaction mixture in a conventional manner, as stated under A.

C: A sulfonamide of the formula V is reacted in a conventional manner (EP-A-141 777 and EP-A-101 670) with about the stoichiometric amount of a phenyl carbamate VI in an inert organic solvent at from 0° to 120° C., preferably from 20° to 100° C. The reaction is carried out continuously or batchwise at atmospheric or superatmospheric pressure (up to 50 bar), preferably at from 1 to 5 bar.

Bases such as tertiary amines, which accelerate the reaction and improve the product quality, may be added here. Suitable bases for this purpose are those stated under A, in particular triethylamine, 2,4,6-collidine, 1,4-diazabicyclo[2.2.2]octane [DABCO] or 1,8-diazabicyclo[5.4.0]undec-7-ene (DBU), in an amount of from 0.01 to 1 mol per mole of starting material V.

Advantageously used solvents or diluents are those stated under A.

The solvent is used in an amount of from 100 to 2,000, preferably from 200 to 700, % by weight, based on the educt V.

The compound V required for the reaction is generally used in about an equimolar amount (for example in an amount of 80 to 120%, based on the particular starting materials VI, of the stoichiometric amount). The starting material VI may be initially taken in one of the abovementioned diluents and the starting material V then added.

However, it is also possible initially to take the starting material V in one of the stated solvents and then to add the carbamate VI. In both cases, one of the stated bases may be added as a catalyst before or during the reaction.

To complete the reaction, stirring is carried out for a further 20 minutes to 24 hours at from 0° to 120° C., preferably from 10° to 100° C., in particular from 20° to 80° C., after the addition of the components.

The sulfonylureas of the formula I are isolated from the reaction mixture by the conventional methods, as described under A.

D: A sulfonamide of the formula V is reacted in a conventional manner (EP-A-234 352) with about the stoichiometris amount of an isocyanate VII in an inert organic solvent at from 0° to 150° C., preferably from 10° to 100° C. The reaction can be carried out continuously or batchwise at atmospheric or superatmospheric pressure (up to 50 bar), preferably at from 1 to 5 bar.

Bases such as tertiary amines, which accelerate the reaction and improve the product quality, may be added before or during the reaction. Suitable bases for this purpose are those stated under A, in particular triethylamine or 2,4,6-collidine, in an amount of from 0.01 to 1 mol per mole of starting material V.

Advantageously used solvents are those stated under A. The solvent is used in an amount of from 100 to 2,000, preferably from 200 to 700, % by weight, based on the educt V.

The compound V required for the reaction is generally used in about the equimolar amount (for example in an amount of from 80 to 120%, based on the educts VII, of the stoichiometric amount). The starting material VII can be initially taken in one of the stated diluents and the starting material V then added. However, it is also possible initially to take the sulfonamide and then to add the isocyanate VII.

To complete the reaction, stirring is carried out for a further 20 minutes to 24 hours at from 0° to 120° C., preferably from 10° to 100° C., in particular from 20° to 80° C., after the addition of the components. The end product I can be obtained from the reaction mixture in a conventional manner, as described under A.

The sulfonyl isocyanates of the formula II which are required as starting materials can be obtained in a conventional manner from the corresponding sulfonamides by phosgenation (Houben-Weyl, 11/2 (1985) 1106 and U.S. Pat. No. 4,379,769) or by reaction of the sulfonamides with chlorosulfonyl isocyanate (German Laid-Open Application DOS 3,132,944).

The sulfonylcarbamates of the formula IV were prepared by, or similarly to, conventional reactions (e.g. EP-A 120 814). However, the sulfonyl isocyanates of the formula II can also be converted into the carbamates of the formula IV in a smooth reaction in an inert solvent, such as ether or dichloromethane.

Carbamates of the formula VI are obtainable by, or similarly to, known reactions (e.g. EP-A 101 670), but they can also be prepared from the corresponding isocyanates VII by reaction with phenol.

The isocyanates of the formula VII are obtained from the amines of the formula III by treatment with oxalyl chloride or phosgene (by a method similar to that described in Angew. Chem. 83 (1971), 407 or EP-A 388 873).

The sulfonamides can be obtained by reacting the corresponding sulfonyl chlorides with ammonia (Houben-Weyl, Methoden der organischen Chemie, Volume 9 (1955), 605). The sulfonyl chlorides are obtained either by a Meerwein reaction (diazotization of suitable amines and sulfochlorination under catalysis with a copper salt) or by chlorosulfonation of suitable aromatics, for example 2,5-dichlorobenzenesulfonyl chloride from p-dichlorobenzene (Houben-Weyl, Methoden der organischen Chemie, Volume 9 (1955), 557 et seq.).

2-Amino-4-methoxy-6-trifluoromethyl-1,3,5-triazine and 2-amino-4-ethoxy-6-trifluoromethyl-1,3,5triazine are known from the literature (Yakugaku Zasshi 95 (1975), 499).

The salts of the compounds I are obtainable in a conventional manner (EP-A 304 282, U.S. Pat. No. 4,599,412). They are obtained by deprotonation of the corresponding sulfonylureas I in water or in an inert organic solvent at from −80° to 120° C., preferably from 0° to 60° C., in the presence of a base.

Examples of suitable bases are alkali metal or alkaline earth metal hydroxides, hydrides, oxides or alcoholates, such as sodium, potassium and lithium hydroxide, sodium methylate, ethylate or tert-butylate, sodium and calcium hydride and calcium oxide.

Examples of suitable solvents in addition to water are also alcohols, such as methanol, ethanol and tert-butanol, ethers, such as tetrahydrofuran and dioxane, acetonitrile, dimethylformamide, ketones, such as acetone and methyl ethyl ketone, and halgenated hydrocarbons.

The deprotonation can be carried out under atmospheric pressure or at up to 50 bar, preferably at from atmospheric pressure to a superatmospheric pressure of 5 bar.

The compounds I or the herbicides containing them, and their environmentally compatible salts of alkali metals and alkaline earth metals, can control weeds very well in crops such as wheat, rice and corn, without damaging the crops, an effect which occurs in particular at low application rates. They can be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure the very fine distribution of the novel active ingredients.

The compounds I are suitable in general for the preparation of directly sprayable solutions, emulsions, pastes or oil dispersions. Suitable inert additives include mineral oil fractions having a medium to high boiling point, such as kerosene or diesel oil, coal tar oils and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates as such dissolved in an oil or solvent can be homogenized in water by means of wetting agents, adherents, dispersants or emulsifiers. However, the concentrates which consist of active ingredient, wetting agent, adherents, dispersants or emulsifiers and possibly solvents or oil and which are suitable for dilution with water can also be prepared.

Suitable surfactants are the alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, the condensates of naphthalene or of naphthalenesulfonic acid with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetal, sorbitol esters, ligninsulfite waste liquors or methylcellulose.

Powders, broadcasting agents or dusting agents can be prepared by mixing and milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, caicium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulose powders and other solid carriers.

The formulations contain in general from 0.1 to 95, preferably from 0.5 to 90, % by weight of active ingredient. Examples of formulations are:

I. 90 parts by weight of compound No. 1 are mixed with 10 parts by weight of N-methyl-α-pyrrolidone and a solution which is suitable for use in the form of very small drops is obtained.

II. 20 parts by weight of compound No. 1 are dissolved in a mixture which consists of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of compound No. 1 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 1 are dissolved in a mixture which consists of 25 parts by weight of cyclohexanone, 65 parts by weight of a mineral oil fraction boiling within a range of from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of active ingredient No. 1 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of a silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1 are mixed with 97 parts by weight of finely divided kaolin. A dusting agent which contains 3% by weight of the active ingredient is obtained in this manner.

VII. 30 parts by weight of active ingredient No. 1 are thoroughly mixed with a mixture of 92 parts by weight of silica gel powder and 8 parts by weight of paraffin, which was sprayed onto the surface of this silica gel. A formulation of the active ingredient having good adhesion is obtained in this manner.

VIII. 20 parts by weight of active ingredient No. 1 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

Application may be effected by the preemergence or postemergence method. If the active ingredients are less well tolerated by certain crops, it is possible to use application methods in which the herbicides are sprayed with the aid of the sprayers in such a way that the leaves of the sensitive crops are as far as possible not affected while the active ingredients reach the leaves of undesirable plants growing underneath or the uncovered soil surface (post-directed, lay-by).

The application rates of active ingredient are from 0.001 to 1.0, preferably from 0.01 to 0.5, kg/ha, depending on the aim of control, the season, the target plants and the stage of growth.

In view of the versatility of the application methods, the novel compounds or agents containing them can also be used in a further number of crops for eliminating undesirable plants. Examples of suitable crops are the following:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica apa var. silvestris | beets |
| Camellia sinensis | tea plants |
| Carthamus tinctorius | safflower |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (luceme) |
| Musa spp. | banana plants |
| Nicotiana tabacum | tobacco |

-continued

| Botanical name | Common name |
| --- | --- |
| (N. rustica) | |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus Spp. | pine trees |
| Pisum sativum | English peas |
| Prunus avium | cherry trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

In order to broaden the action spectrum and to achieve synergistic effects, the triazinyl-substituted sulfonylureas of the formula I can be mixed with many members of other groups of herbicidal or growth-regulating active ingredients and applied together with them. Examples of suitable components of the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, phenoxy- and hetaryloxyphenylpropionic acids and their salts, esters and amides and others.

It may also be advantageous to apply the compounds of the formula I, alone or in combination with other herbicides, also as a mixture with further crop protection agents, for example with pesticides or agents for controlling phytopathogenic fungi or bactericides. The miscibility with mineral salt solutions which are used for eliminating nutrient and trace element deficiencies is also of interest. Nonphytotoxic oils and oil concentrates may also be added.

Examples of the synthesis of the compounds I are given below.

1) 2-Chloro-1-N-[4-methoxy-6-trifluoromethyl-1,3,5-triazin-2-yl)-aminocarbonyl]-benzenesulfonamide

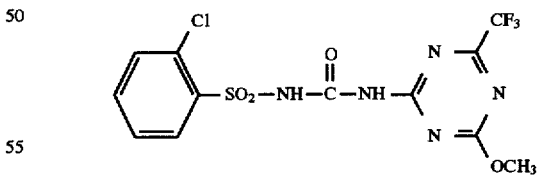

4.5 g (21 mmol) of 2-chlorobenzenesulfonyl isocyanate were added to a solution of 4.0 g (21 mmol) of 2-amino-4-methoxy-6-trifluoromethyl-1,3,5-triazine in 20 ml of acetonitrile at 25° C. The solution thus obtained was stirred for 21 hours at 25° C. The solvent was then removed under reduced pressure at 40° C. and the solid residue was stirred vigorously for 3 hours with 11 of a diethyl ether/hexane mixture (v/v 1:1). The product was filtered off under suction and dried under reduced pressure at 40° C. 6.5 g (75% of theory) of the title compound of melting point 166°–168° C. were obtained.

2) Sodium 2-chloro-1-N-[(4-methoxy-6-trifluoromethyl-1,3,5-triazin-2-yl)-aminocarbonyl]-benzenesulfonamide 0.66 g (3.6 mmol) of a solution of sodium ethoxide (30% strength by weight) in methanol was added to a suspension of 1.5 g (3.6 mmol) of 2-chloro-1-[(4-methoxy-6-trifluoromethyl-1,3,5-triazin-2-yl)-aminocarbonyl]-benzenesulfonamide in 10 ml of methylene chloride at 25° C. The resulting homogeneous solution was stirred for 1 hour at 25° C. After removal of the volatile components at 60° C. under reduced pressure from a water pump, the title compound was obtained in quantitative yield, its decomposition point being 220°–224° C.

The active ingredients stated in Table 1 below are obtained by a similar preparation method.

TABLE 1

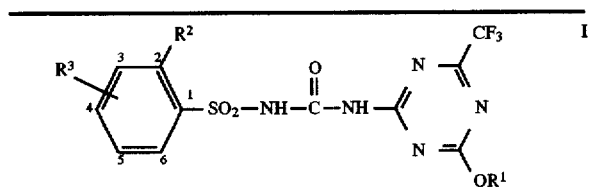

| Active ingredient no. | $R^1$ | $R^2$ | $R^3$ | mp. [°C.] |
|---|---|---|---|---|
| 1 | $CH_3$ | Cl | H | 166–168 |
| 2 | $CH_3$ | $O(CH_2)_2OCH_3$ | H | 108–110 |
| 3 | $CH_3$ | $CF_3$ | H | 164–169 |
| 4 | $CH_3$ | Cl | H | 220–224 (decomp.) Na salt |
| 5 | $CH_3$ | $O(CH_2)_2OCH_3$ | H | 119 (decomp.) Na salt |
| 6 | $CH_3$ | $O(CH_2)_2OCH_3$ | H | 139 (decomp.) Ca salt |
| 7 | $CH_3$ | $CF_3$ | H | 165 (decomp.) Na salt |
| 8 | $CH_3$ | Cl | 6-Cl | 168 |
| 9 | $CH_3$ | Cl | H | 160–163 (decomp.) Ca salt |
| 10 | $CH_3$ | Cl | H | 232 (decomp.) K salt |
| 11 | $CH_3$ | Cl | 6-$CH_3$ | 140–144 |
| 12 | $CH_3$ | Cl | 5-Cl | 151–156 |
| 13 | $CH_3$ | F | H | 162–164 |
| 14 | $CH_3$ | Br | H | 156–160 |
| 15 | $CH_3$ | J | H | |
| 16 | $CH_3$ | F | H | >220 (decomp.) Na salt |
| 17 | $CH_3$ | F | H | >220 (decomp.) K salt |
| 18 | $CH_3$ | F | H | >220 (decomp.) Ca salt |
| 19 | $CH_3$ | F | 6-F | 177–180 |
| 20 | $CH_3$ | F | 6-F | 180–200 (decomp.) Na salt |
| 21 | $CH_3$ | F | 6-F | >220 (decomp.) K salt |
| 22 | $CH_3$ | F | 6-F | 155–159 (decomp.) Ca salt |
| 23 | $C_2H_5$ | Cl | 3-Cl | 155–157 |
| 24 | $CH_3$ | Cl | 3-Cl | 175–177 |
| 25 | $C_2H_5$ | Cl | 3-Cl | 197–200 (decomp.) Na salt |
| 26 | $CH_3$ | Cl | 3-Cl | 198–201 (decomp.) Na salt |
| 27 | $CH_3$ | Cl | 6-$CH_3$ | 175–178 (decomp.) Na salt |
| 28 | $CH_3$ | Cl | 6-$CH_3$ | 180–183 K salt |
| 29 | $CH_3$ | $SO_2CH_3$ | H | 176–177 |
| 30 | $CH_3$ | $SO_2CH_3$ | H | 186–183 Na salt |
| 31 | $CH_3$ | Cl | 3-Cl | >220 (decomp.) K salt |
| 32 | $C_2H_5$ | $SO_2CH_3$ | H | 164–165 |
| 33 | $C_2H_5$ | Cl | H | 149–151 |

TABLE 1-continued

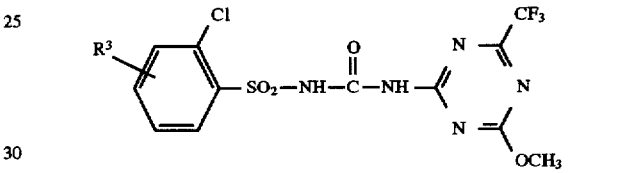

| Active ingredient no. | $R^1$ | $R^2$ | $R^3$ | mp. [°C.] |
|---|---|---|---|---|
| 34 | $CH_3$ | $CF_3$ | 6-$CH_3$ | 149–150 |
| 35 | $CH_3$ | $CH_3$ | 6-$CH_3$ | 200 (decomp.) Na salt |
| 36 | $CH_3$ | $CF_3$ | H | 211 (decomp.) Ca salt |
| 37 | $CH_3$ | $SO_2C_2H_5$ | H | 152–155 |
| 38 | $CH_3$ | $SO_2$-n-$C_3H_7$ | H | 181–182 |
| 39 | $CH_3$ | $SO_2$-i-$C_3H_7$ | H | 173–177 |

The compounds mentioned below can also be obtained in a similar manner:

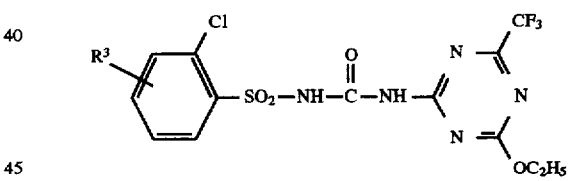

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy;

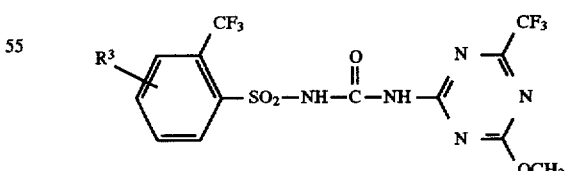

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy;

or the sodium salts thereof, where $R^3$ is hydrogen, 3-methyl, 4-methyl, 5 -methyl, 6 -methyl, 3-ethyl, 4-ethyl, 5-ethyl, 6-ethyl, 3-fluoro, 4-fluoro, 5-fluoro, 6-fluoro, 3-chloro, 4 -chloro, 5 -chloro, 6 -chloro, 3-methoxy, 4-methoxy, 5-methoxy, 6-methoxy, 3-ethoxy, 4-ethoxy, 5-ethoxy or 6-ethoxy;

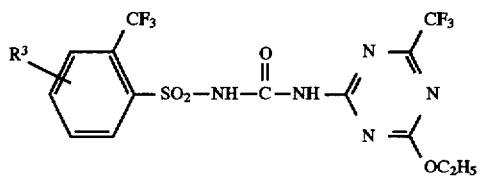

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy;

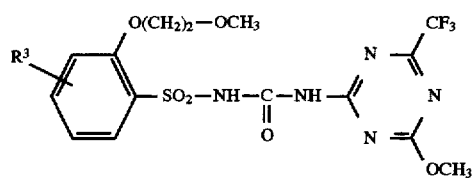

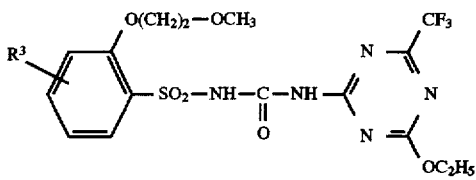

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy;

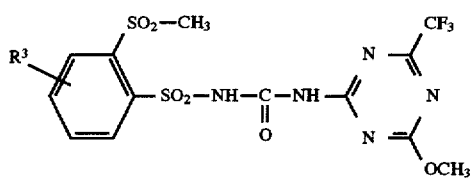

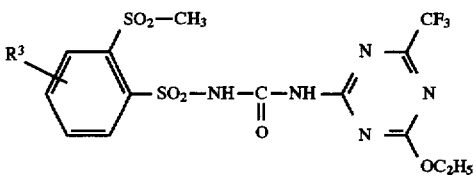

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy;

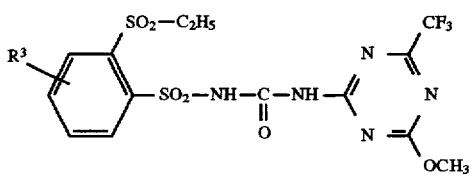

-continued

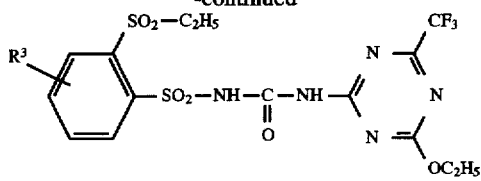

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy;

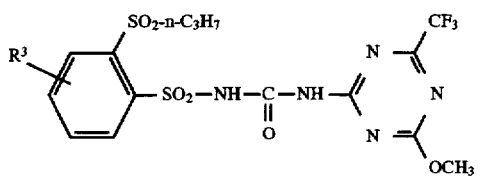

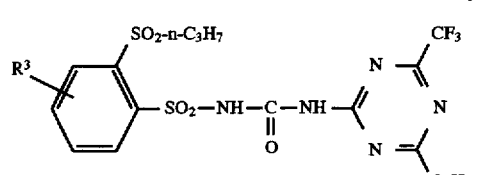

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy;

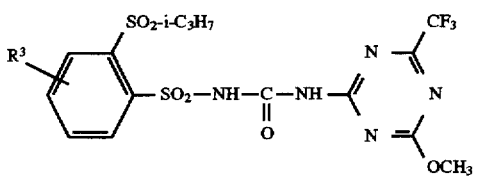

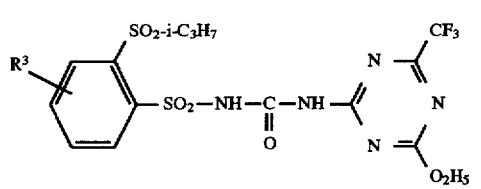

or the sodium salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy or 6-ethoxy.

Use Examples:

The herbicidal action of the N-[(1,3,5-triazin-2-yl)-aminocarbonyl]-benzenesulfonamide of the formula I on the growth of the test plants is demonstrated by the following greenhouse experiments.

The culture vessels used are plastic flower pots having a capacity of 300 cm$^3$ and containing loamy sand with about 3.0% of humus as the substrate. The seeds of the test plants are sown shallowly and separately according to species.

For the purposes of the postemergence treatment, either directly sown plants or plants grown in the same vessels are selected, or they are first grown separately as seedlings and transplanted into the test vessels a few days before the treatment.

The test plants are then treated, at a height of growth of from 3 to 15 cm depending on the form of growth, with the active ingredients suspended or emulsified in water as a distributing agent, said active ingredients being sprayed through finely distributing nozzles. The application rate for the postemergence treatment is 0.06 or 0.03 kg/ha of a.i. (active ingredient).

The test vessels are placed in a greenhouse, warmer areas (from 20° to 35° C.) being preferred for warmth-loving species and from 10° to 20° C. for those from temperate climates. The test period extends over from 2 to 4 weeks. During this time, the plants are tended and their reactions to the individual treatments are evaluated.

Evaluation is based on a scale from 0 to 100. 100 means no emergence of the plants or complete destruction of at least the above-ground parts and 0 means no damage or normal course of growth.

The plants used in the greenhouse experiments consist of the following species:

| Botanical name | Common name |
| --- | --- |
| Amaranthus retroflexus | redroot pigweed |
| Chenopodium album | common lambsquarters |
| Chrysanthemum | oxeye daisy |
| Galium aparine | catchweed bedstraw |
| Stellaria media | chickweed |
| Triticum aestivum | summer wheat |
| Zea mays | corn |

When 0.06 or 0.03 kg/ha of a.i. are used in the postemergence method, broad-leaved undesirable plants can be very well controlled with Example No. 1, with simultaneous excellent selectivity in wheat and corn.

Results from biological investigations in which the novel active ingredient of Example 1 was compared with the compound B disclosed in U.S. Pat. No. 4,169,719 are summarized in the Table below.

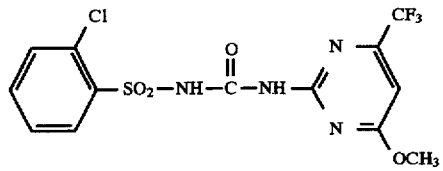

TABLE 1

Comparison of the herbicidal activity of Example compound No. 1 with comparative compound B during postemergence application of 0.06 or 0.03 kg/ha a.i. in the greenhouse

| | Damage [%] Application rate [kg/ha a.i.] | | | |
| --- | --- | --- | --- | --- |
| | Example 1 | | B | |
| Test plants | 0.06 | 0.03 | 0.06 | 0.03 |
| Amaranthus retroflexus | 100 | 100 | 0 | 0 |
| Galium aparine | 95 | 90 | 0 | 0 |
| Chenopodium album | 90 | 90 | 0 | 0 |

In Tables 2 and 3, the novel compounds of Examples 1 and 3 are compared with the comparative substances G and H disclosed in U.S. Pat. No. 4,127,405.

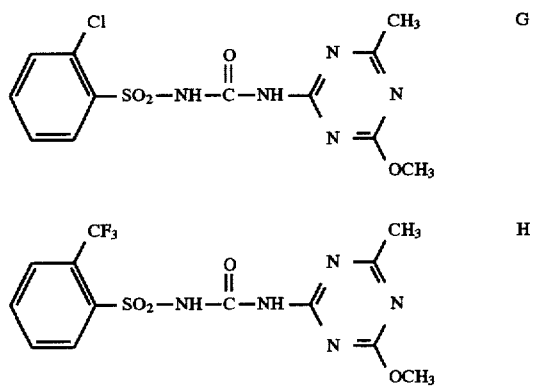

The experimental results clearly demonstrate the surprisingly high selectivities.

The known compounds cause unacceptable damage of 85 and 70%, respectively, in corn. In contrast, Example compounds 1 and 3 exhibit only 10% damage to the crop and have an identical or better herbicidal action.

TABLE 2

Comparison of the herbicidal activity of Example compound No. 1 with comparative compound G in postemergence application of 0.03 kg/ha a.i. in the greenhouse

| | Damage [%] | |
| --- | --- | --- |
| Test plants | Example 1 | G |
| Corn | 10 | 85 |
| Undesirable plants: | | |
| Amaranthus retroflexus | 90 | 90 |
| Galium aparine | 80 | 74 |

TABLE 3

Comparison of the herbicidal activity of Example compound No. 3 with comparative compound H in postemergence application of 0.06 or 0.03 kg/ha a.i. in the greenhouse

| | Damage [%] Application rate [kg/ha a.i.] | | | |
| --- | --- | --- | --- | --- |
| | Example 3 | | H | |
| Test plants | 0.06 | 0.03 | 0.06 | 0.03 |
| Corn | 10 | 10 | 70 | 70 |
| Undesirable plants: | | | | |
| Amaranthus retroflexus | 90 | 90 | 90 | 90 |
| Galium aparine | 95 | 60 | 10 | 0 |
| Chenopodium album | 98 | 98 | 98 | 98 |
| Sinapis alba | 95 | 90 | 90 | 90 |

Excellent selectivities in the sensitive Example crop rice, summer wheat and corn are achieved by the novel compound No. 7, as shown by the results summarized in Tables 4 and 5 below.

TABLE 4

Control of undesirable broad-leaved plants in conjunction with toleration by the Example crops summer wheat and corn in postemergence application of 0.015 kg of a.i./ha of compound No. 7 in the greenhouse

| Test plants | Damage [%] |
| --- | --- |
| Triticum aestivum | 10 |
| Corn | 15 |
| Undesirable plants: | |
| Amaranthus retroflexus | 90 |
| Chenopodium album | 75 |
| Stellaria media | 100 |

TABLE 5

Control of undesirable broad-leaved plants in conjunction with toleration by the Example crop rice in postemergence application of 0.015 kg of a.i./ha of compound No. 7 in the greenhouse

| Test plants | Damage [%] |
| --- | --- |
| Oryza sativa | 10 |
| Undesirable plants: | |
| Amaranthus retroflexus | 95 |
| Sinapis alba | 70 |
| Stellaria media | 100 |

In a further test, the sodium salt of comparative compound H is compared with Example 7. The results are summarized in Table 6.

TABLE 6

Comparison of the herbicidal activity of Example compound No. 7 with the sodium salt of comparative compound H in postemergence application of 0.06 or 0.03 kg/ha of a.i. in the greenhouse

| | Damage [%] | | | |
| --- | --- | --- | --- | --- |
| | Application rate [kg/ha a.i.] | | | |
| | Example 7 | | H Na salt | |
| Test plants | 0.06 | 0.03 | 0.06 | 0.03 |
| Corn | 10 | 0 | 100 | 100 |
| Undesirable plants: | | | | |
| Amaranthus retroflexus | 100 | 100 | 90 | 90 |
| Galium aparine | 98 | 98 | 70 | 60 |
| Chenopodium album | 100 | 100 | 100 | 100 |

The test results clearly demonstrate the surprisingly high selectivity in conjunction with excellent herbicidal activity of the novel compound.

We claim:

1. An N-((1,3,5-triazin-2-yl)-aminocarbonyl) benzenesulfonamide of the formula I

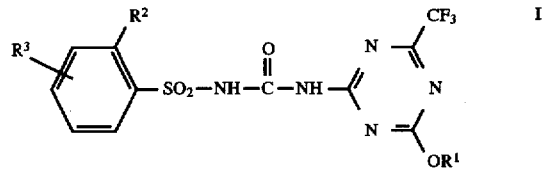

where $R^2$ is methyl, $R^2$ is chlorine and $R^3$ is hydrogen, or its agriculturally useful salts.

2. A herbicidal composition containing a herbicidally effective amount of N-((1,3,5-triazin-2-yl)-aminocarbonyl)-benzenesulfonamide of the formula I as defined in claim 1 or its salt and conventional carriers.

3. A method for controlling undesirable plant growth, wherein a herbicidal amount of an N-[(1,3,5-triazin-2-yl)-amminocarbonyl]-benzenesulfonamide of the formula I as defined in claim 1 or of one of its salts is allowed to act on the plants and/or their habitat.

* * * * *

UNITED STATES PATENT AND TRADEMARK OFFICE
CERTIFICATE OF CORRECTION

PATENT NO.: 5,635,450

DATED: June 3, 1997

INVENTOR(S): MAYER et al.

It is certified that error appears in the above-identified patent and that said Letters Patent is hereby corrected as shown below:

Column 18, claim 1, line 34, "$R^2$ is methyl" should be --$R^1$ is methyl--.

Column 18, claim 3, line 43, "amminocarbonyl" should be --aminocarbonyl--.

Signed and Sealed this

Nineteenth Day of August, 1997

Attest:

BRUCE LEHMAN

Attesting Officer

Commissioner of Patents and Trademarks